United States Patent [19]

Schaedlich et al.

[11] Patent Number: 5,597,535

[45] Date of Patent: Jan. 28, 1997

[54] APPARATUS FOR DETECTING MERCURY

[75] Inventors: Frank H. Schaedlich, Toronto; Daniel R. Schneeberger, Scarborough, both of Canada

[73] Assignee: Tekran Inc., Toronto, Canada

[21] Appl. No.: 201,949

[22] Filed: Feb. 25, 1994

[51] Int. Cl.⁶ .................................................. G01N 1/40
[52] U.S. Cl. ............................. 422/88; 422/91; 422/116; 436/81; 73/1 G
[58] Field of Search .............................. 422/88, 91, 93, 422/116, 119; 73/1 G; 436/81

[56] References Cited

U.S. PATENT DOCUMENTS

| | | | |
|---|---|---|---|
| 3,884,639 | 5/1975 | Sugiyama et al. | 436/81 |
| 4,023,929 | 5/1977 | Becker et al. | 436/81 |
| 4,151,737 | 5/1979 | Breuer et al. | 73/1 G |
| 4,531,398 | 7/1985 | Di Benedetto et al. | 73/1 G |
| 5,026,652 | 6/1991 | Huber | 436/81 |

OTHER PUBLICATIONS

Oct. 1991 Monitoring mercury levels in the environment: Application of a fluorescence approach for sub–PPB and PPT Levels By: P. B. Stockwell et al.

1991 Monitoring elemental mercury in an urban environment By: P. B. Stockwell et al. [Process Control and Quality, 1(1991) 293–296 Elsevier Science Publishers B.V., Amsterdam].

*Primary Examiner*—Jeffrey R. Snay
*Attorney, Agent, or Firm*—Bereskin & Parr

[57] ABSTRACT

Mercury Detection Method and Apparatus utilizes cartridges including gold for adsorbing mercury as an amalgam. The adsorbed mercury is desorbed by heating and passed through a Cold Vapour Atomic Fluorescence Spectrophotometer. Each cartridge is flushed with an inert gas, so that air and contaminants are never passed directly through the detector, so only inert gas passes through it. To further prevent adsorption of contaminants, the cartridges are maintained at a minimum temperature, above ambient temperature and below 100° C. To enable unattended calibration, a permeation source is provided having a permeation chamber and a valve assembly, including 3 separate valves, to ensure that in an off state mercury vapour cannot leak to the cartridges. To ensure an efficient use of the inert gas, its flow can be adjusted between 3 different levels, for flushing, desorption of mercury, and an idle state to maintain the apparatus purged air.

19 Claims, 4 Drawing Sheets

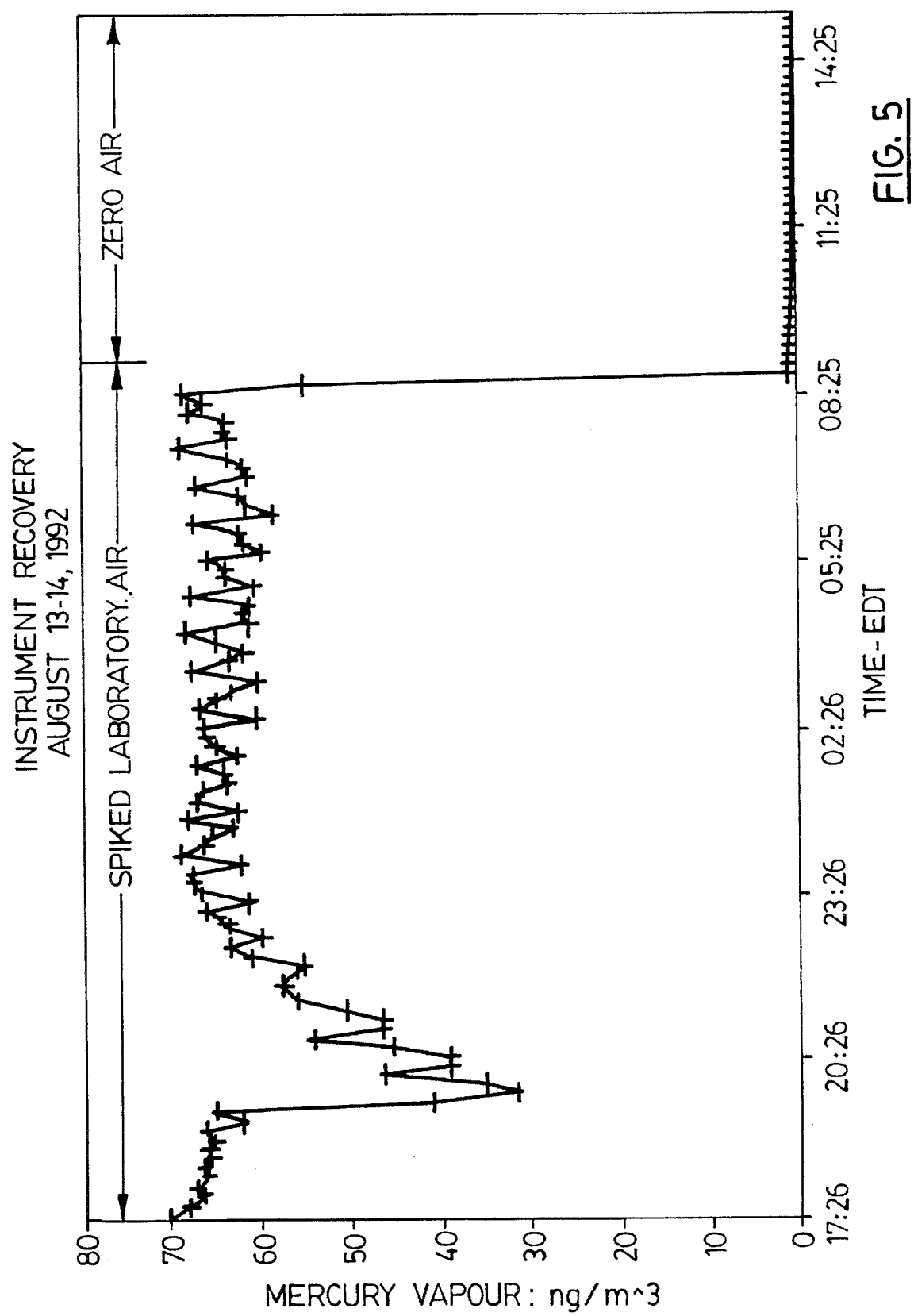

APPARATUS FOR DETECTING MERCURY

FIELD OF THE INVENTION

This invention relates to the detection of mercury. This invention more particularly relates to the detection of mercury in air, and to a method and apparatus capable of providing a low detection limit.

BACKGROUND OF THE INVENTION

There are many known methods of mercury analysis, including: colorimetric; atomic absorption coupled to vapour generation; atomic absorption following gold trapping from vapour generation; and atomic fluorescence coupled to vapour generator.

Atomic fluorescence is commonly achieved in a Cold Vapour Atomic Fluorescence Spectrophotometer (CVAFS). CVAFS is preferred, as compared to atomic absorption, since the phenomena is linear over a much wider range and is not subject to positive interferences. Rather, it can be subject to negative interference modes, with certain molecular species causing quenching. The present invention provides techniques for improving the performance of such a device and for overcoming negative interference.

It is known that gold is an excellent adsorber of mercury, which forms a gold amalgam with mercury. However, many conventional instruments suffer from a "memory" effect. This arises due to the use of gold having substantial thickness in a detector cell, and mercury migrating from the surface of the gold to the interior, or at least below the surface. Consequently, when the mercury is flushed from a detector cell by heating in an inert gas flow, in known manner, not all the mercury is immediately released. In subsequent cycles, mercury from below the gold surface can migrate to the surface and be flushed out, giving a false mercury reading. While it has been proposed to use such materials as gold-coated sand, with the intention of providing a gold film so thin as to prevent this problem, such technique has its own drawbacks. The gold-coated sand is not always completely stable, and the gold may not remain plated or adhered to the sand particles, particularly when subjected to hundreds and thousands of heating and cooling cycles.

Pure gold is very selective and does not adsorb most contaminants that can give false readings, which may contaminate the flow path of the instrument. However, problems have often been reported with the adsorption of competing compounds. Thus, the activity of the gold can be taken up by other compounds, and once used, the gold in the cartridge will not be able to capture mercury. This will give a false, low reading. During desorption, the competing compounds may be released. They may then register a false positive reading, attenuate the actual mercury signal, or contaminate the flow path. Organic compounds and water vapour are common examples of contaminants that can be unintentionally entrained.

In conventional instruments, the flows of different gases, such as air, carrier gas, are not controlled so as to give optimum performance. No consideration has been given to optimizing the flows of such gases.

In many conventional instruments, ambient air and other contaminants can be passed through the detector cell. To maintain the purity of the detector cell, and prevent contamination, it is desirable that only a carrier gas, containing mercury when present, be passed through the detector cell.

Common types of detector cells have the interior optical path filled with air. The ultraviolet radiation produced by the lamp of the detector produce compounds in air which absorb the ultraviolet light. The most important reaction is the break down of oxygen and the creation of free radicals that recombine to produce ozone. These UV adsorbent compounds decrease sensitivity of the detector and cause significant baseline shift.

To calibrate known instruments, it is necessary to provide manual injections using gas tight syringes. This is cumbersome and awkward, and necessarily prevents any automation of the device.

Accordingly, it is desirable to provide a mercury detector, based on Cold Vapour Atomic Fluorescence Spectrophotometry which provides a much higher degree of sensitivity. It is desirable that such a detector not suffer from any memory effects of the gold, and not be susceptible to contaminants entering the detector cartridges. It is desirable that the gas flows be controlled to optimise, or at least improve, usage of the gases and performance of the apparatus as a whole.

It is further desirable that the apparatus be capable of automatic operation, and include means for automatic recalibration.

It is also desirable that the detector itself not be susceptible to the generation of ultraviolet absorbent compounds which would decrease sensitivity.

SUMMARY OF THE PRESENT INVENTION

In accordance which the present invention, there is provided a mercury detection apparatus comprising: a main carrier gas inlet; a sample gas inlet; inlet valve means connected to the carrier gas and sample gas inlets; a cartridge including gold, for accumulating mercury as an amalgam, connected to the inlet valve means; an outlet valve means connected to the cartridge; a sample gas flow path extending through from the sample gas inlet through the outlet and outlet valve means and through the cartridge; a pump for pumping sample air through the cartridge in the sample gas path; a vent connected to the outlet valve means; and a mercury detector connected to the outlet valve means; and a control unit connected to the inlet and outlet valve means to control thereof, wherein with the sample gas inlet and the pump connected to the cartridge by the inlet and outlet valve means, the pump draws sample air through the cartridge, and with the carrier gas inlet connected by the inlet valve means to the cartridge, the outlet valve means selectively connects the cartridge to one of the vent, for venting residual air, and to the detector for detection of any mercury. The apparatus includes a vent three-way valve connected to the outlet valve means, and to both the detector and the vent.

Another aspect of the present invention provides an apparatus for detecting mercury, the apparatus comprising: a carrier gas inlet; a sample gas inlet; an inlet valve means connected to the carrier gas and sample gas inlets; at least one cartridge containing gold for accumulation of mercury, connected to the inlet valve means; an outlet valve means connected to each cartridge; a sample gas flow path extending from the sample gas inlet through the inlet and outlet value means and through each cartridge; a pump in the sample gas flow path; a detector connected to the outlet valve means; and a heater means for heating each cartridge; and a control unit connected to and controlling the inlet valve means, the outlet valve, the pump, the detector and the heating means, the heating means being controllable to maintain the cartridges at a temperature above ambient temperature and below around 100° C., to prevent adsorption of contaminants.

The present invention further provides a permeation source, for use with mercury detection apparatus, the permeation source comprising a permeation chamber having a chamber inlet and a chamber outlet; a mercury permeation source within the permeation chamber; a heating unit for maintaining the permeation chamber at a substantially constant temperature; valve means having an inlet for carrier gas and an inlet connected to the permeation chamber outlet, a permeation source output and a permeation source vent; and a secondary carrier gas inlet connected to the permeation chamber and the inlet of the valve means.

The provision of a permeation source enables the device to operate automatically, and enables automatic, unattended recalibration as required.

Preferably, inert gas is conserved, by setting different flow rates for different purposes, more preferably, there are 3 separate flow rates. The cartridges are flushed with carrier gas at a first relatively high flow rate; during entrainment of mercury vapour, carrier gas is set at a second, relatively low flow rate; and, during idle or inactive periods, the carrier gas flow is maintained at a third flow rate, below the first and second flow rates, sufficient to maintain the apparatus purged of air. This serves to conserve and make optimal use of an inert gas supply.

DESCRIPTION OF DRAWING FIGURES

For a better understanding of the present invention and to show more clearly how it may be carried into effect, reference will now be made, by way of example to the accompanying drawings, which show a preferred embodiment of the present invention and in which:

FIG. 5 is a graph showing a recovery characteristic of the apparatus.

DESCRIPTION OF PREFERRED EMBODIMENT

Figure 1:
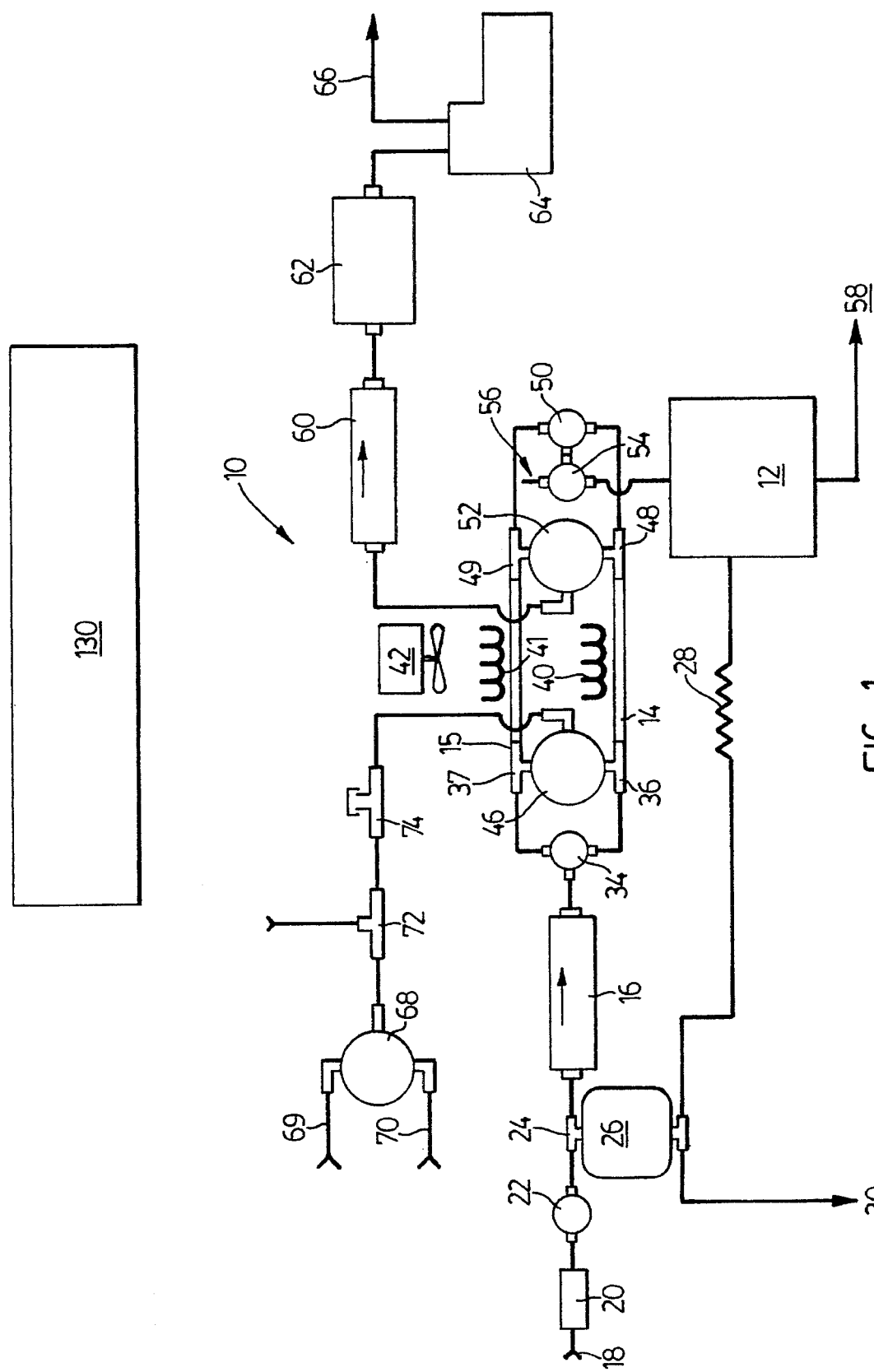
FIG. 1 is a schematic flow diagram of an apparatus in accordance with the present invention.

The apparatus as a whole is indicated by the reference 10. The apparatus 10 includes a detector 12 first and second adsorbent cartridges 14, 15, and a mass flow controller 16.

Figure 4:
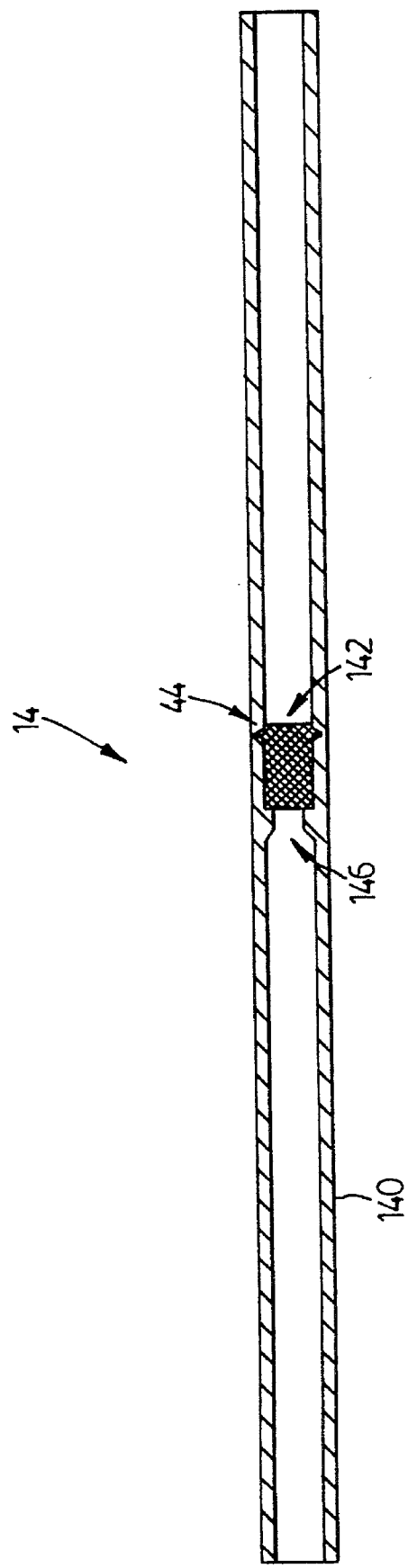
FIG. 4 is a sectional view through a sampling cartridge.

The structure of each cartridge is shown in detail in FIG. 4. Each cartridge 14, 15 comprises a quartz glass tube 140 having a 6 mm outside diameter and a 4 mm inside diameter. A pure gold screen disk assembly is indicated at 142. The tube 140 provides a retention groove at 144 and defines a flow sealing orifice 146, which also serves to retain the gold disk assembly in position. The gold disk assembly comprises 100 disks, and is approximately 8 mm long with a 4 mm diameter. Total gold surface area is approximately 17.7 cm$^2$.

A carrier gas inlet 18 is connected through an inlet filter 20, located at an inlet bulkhead, and then through a stainless steel cutoff valve 22.

This valve 22 automatically turns the carrier gas supply on and off as power is supplied, to prevent waste of carrier gas during a power failure and when the instrument is turned off.

At 24, a T connector splits the flow into two streams. One stream is delivered to a precision pressure regulator 26. The regulator 26 in turn has an outlet, connected by the T connector to a flow restrictor 28 for a purge flow for the detector and to a permeation source 30, shown in detail in FIG. 2.

The pressure regulator 26 provides a fixed pressure that is applied to the flow restrictor 28, so as to give a fixed, lower rate of flow. Here, it is approximately 10 ml/min., to the optical path of the detector 12, shown in FIG. 3 and described in greater detail below.

The other stream from the T connector 24 is connected to the mass flow controller 16, as is explained in greater detail below, the mass flow controller 16 is capable of setting different flow levels, so as to give greatly reduced carrier gas usage and shorter cycle times. The following levels could be set:

during an initial flush phase of a detector cycle, the controller is set to allow a large carrier gas flow, to allow a rapid flushing of air out of the cartridge and surrounding fittings, thereby allowing quicker cycling;

during baseline and peak acquisition, the carrier flow is set so as to produce optimally shaped peaks; and during idle periods, the flow is set for a low value, which is just sufficient to keep the lines and detector itself flushed and stable.

The outlet of the mass flow controller 16 is connected to a first, inlet valve 34, a three-way solenoid valve 34, which in turn is connected by T connectors 36 and 37, to the first and second cartridges 14 and 15. Each cartridge is provided with a gold absorbent in a form of a fine wire screen. The quantity of gold used and the configuration of the wire screen is as such to ensure that the active surface area is sufficiently large. Each cartridge is also provided with a respective heater 40, 41 and a common cooling fan indicated schematically at 42. The function of these components is detailed below.

Pure gold is used, instead of sand or glass beads coated with gold, since it is able to endure hundreds of thousands of heating cycles without breaking down.

The T connectors 36, 37 are also connected to a second inlet three-way valve 46.

The outlets of the cartridges 14, 15 are connected through outlet T connectors 48, 49 to a first outlet three-way valve 50. The T connectors 48, 49 are also connected to a second, outlet three-way valve 52.

The first and second inlet and outlet valves 34, 6, 50 and 52 are all three-way solenoid valves.

The first outlet valve 50 is further connected to a vent three-way valve 54, which has one outlet connected to a vent indicated at 56 and on other outlet connected to the detector 12. The detector in turn has a detector vent 58.

The second inlet and outlet valves 46 and 52, as indicated schematically, are larger than the valves 34 and 50, so as to be capable of handling a greater flow rate.

The second outlet valve 52 is connected to a precision mass flow meter 60, which is used to measure mass flow through each cartridge. The mass flow meter 60 is connected through a buffer tank 62 and a sample pump 64 to a pump exhaust 66.

A source selection valve 68 has an inlet 69 for zero air and an inlet 70 for sample air. It is connected through first and second inlet T connectors 72, 74. The first inlet T connector 72 is connected to an outlet of a permeation source detailed below, while the second inlet 74 provides an injection port.

Figure 2:
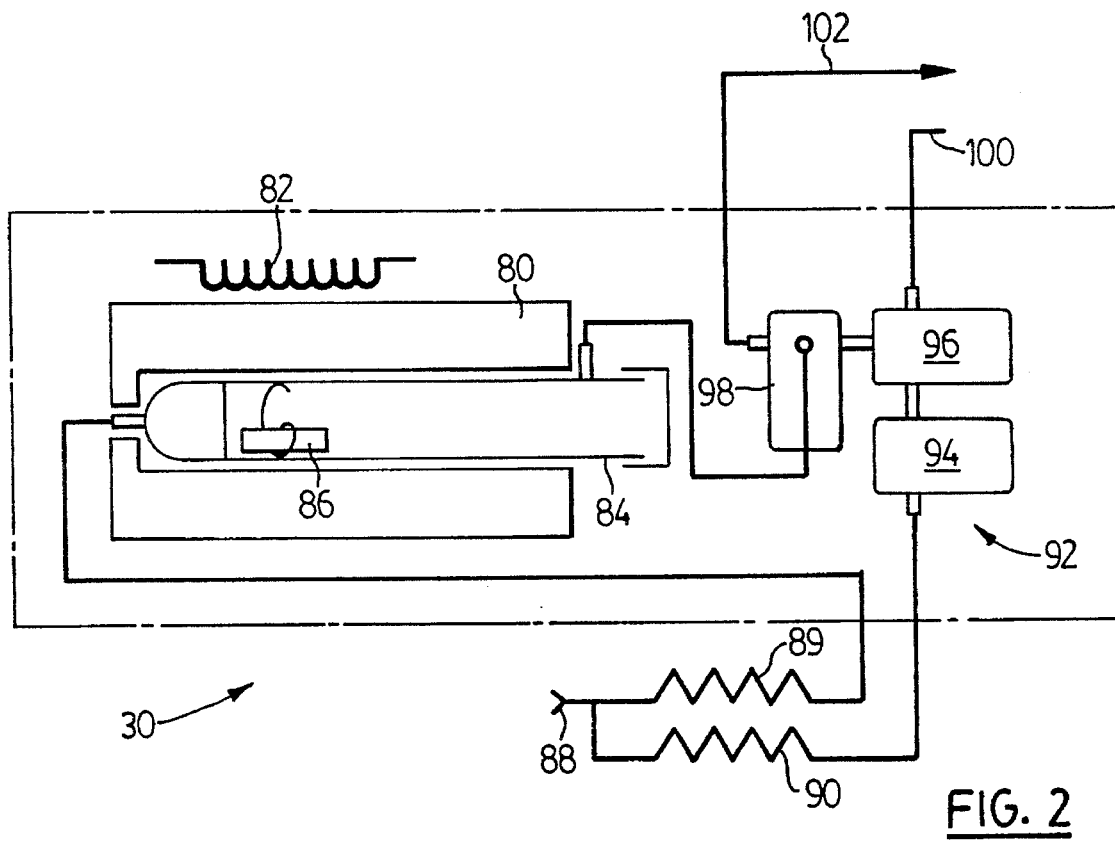
FIG. 2 is a schematic diagram of a permeation source of the apparatus of FIG. 1.

Referring to FIG. 2, this shows, in greater detail, the permeation source 30, which provides a stable, repeatable alternative to calibration by manual injection. An aluminium block 80 is provided with a block heater 82. The block 80 is intended to provide significant thermal inertia, so that the interior of the block is maintained close to desired temperature set point, within 0.05° C.

Within the block 80, there is a permeation chamber 84. Within the chamber 84, a permeation tube 86, which can be conventional, and which is retained by a spring.

A permeation inlet 88 is connected through flow restrictors 89 and 90 to the permeation chamber 84 and a valve assembly indicated at 92.

The valve assembly 92 includes a permeation shut-off valve 94 connected to a first permeation control valve 96. The valve 96 is a specialized fast flush solenoid valve, which is connected to a second permeation control valve 98 and a permeation outlet 100, which is connected to the T connector 72. The valve 96 has a straight through gas path connected between valve 94 and the source output 100. The connection to valve 98 is an injection input which can be closed or opened to inject mercury to the through gas path.

The second permeation control valve 98 is a three-way valve, having an inlet connected to an outlet of the permeation chamber 84, and a further outlet connected to a permeation vent indicated at 102.

The permeation chamber 84 can be provided with different sizes of permeation tubes. These could range, for example, in length from 1–3 cm. The temperature in the permeation chamber can be varied between 45°–100° C., with 50° C. being a normal setting.

As shown in FIG. 1, the permeation inlet 88 is connected to the carrier gas inlet 18, for an inert gas, which in this embodiment is argon. Inert gas is used to provide a continuous purge through the permeation source 30, so as to prevent contamination and eliminate any possibility of oxidation within the permeation tube.

Figure 3:
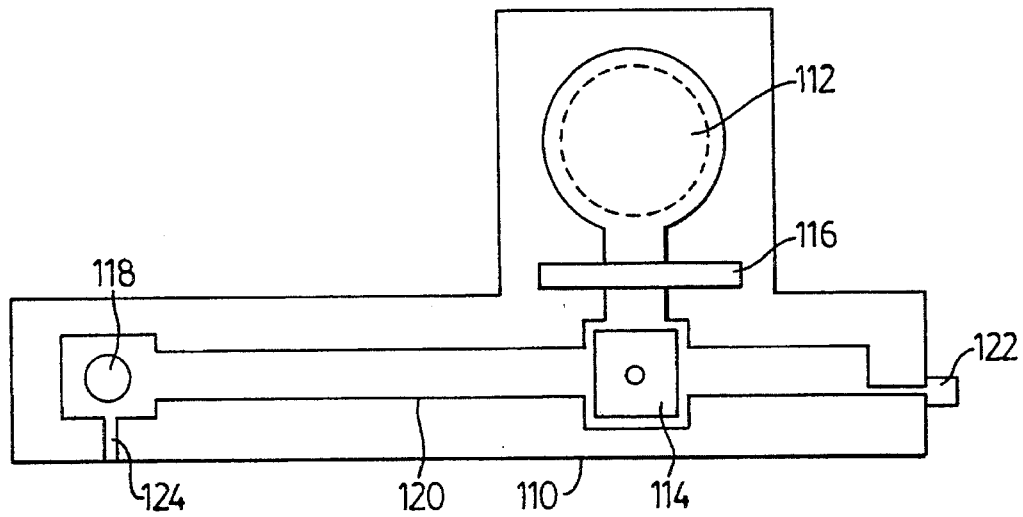
FIG. 3 is a schematic diagram of a detector of the apparatus of FIG. 1.

Referring to FIG. 3, the detector 12 has a housing 110. Within the housing 110, there are the various elements of the detector 12, which can be largely conventional.

Thus, there is a photomultiplier tube 112 and a sample cuvette 114. An interference filter 116 is placed between them. An ultraviolet lamp 118 provides the source of UV radiation.

The components 112–118 are enclosed, at least partially, by an inner housing 120. This defines optical paths from the lamp 118 to the cuvette 114, and in turn from the cuvette 114 to the photomultiplier 112.

An optical path purge inlet 122 is provided at one end, and an optical path outlet 124 is provided at the outlet. As shown in FIG. 1, the flow restrictor 28 is connected to the inlet 122. This ensures that the optical path is continuously purged with a flow of inert gas. This avoids quenching by certain molecular species generated by the UV radiation.

The entire sample path is ¼" OD Teflon, except for the cartridges 14, 15 which are quartz glass. This size is required due to the high sample flow rates. The carrier gas components are ⅛" OD, thick walled Teflon and small bore miniature Teflon solenoid valves in order to minimize dead volume, especially between the cartridges 14, 15 and the detector 12.

The detector uses Cold Vapour Atomic Fluorescence Spectrophotometry (CVAFS), to detect the mercury. Mercury that passes into cuvette 114 is illuminated by the ultraviolet lamp 118, which is a low pressure mercury vapour lamp. Radiation at 253.7 nm excites any mercury atoms present, which fluoresce and re-radiate at the same frequency. The photomultiplier tube 112 is at a right angle to the incident light from the lamp 118, and receives some of this re-radiated light, but not the direct radiation from the lamp 118.

As indicated schematically at 130, a control circuit is connected to various elements of the apparatus, namely the valves 22, 34, 46, 50, 52, 54, 68, 94, 96 and 98, heaters 40 and 41 and fan 42, the detector 12, the mass flow controller 16, the mass flow meter 60, and the sample pump 64. The control circuit includes an embedded microprocessor, which can allow a wide range of features. It can be provided with a suitable interface, including, for example, a keyboard and display. The control circuit 130 can be provided with two or more analog outputs, programmable for selective instrument readings, a serial RS232 port, and digital outputs. Other inputs can be provided as desired.

The microprocessor and the control circuit can include a memory that allows the analyzer to retain information, even in the absence of power, including information or data on instrument settings from parameters from a recent result, and two or more set measurement cycles.

The precision mass flow meter 60 is used to measure sample flow rate through one cartridge 14, 15. The microprocessor integrates flow rate over time, to determine total volume of air or other gas passing through the cartridge.

The speed of the sample pump 64 is controlled by a closed loop feed back controller, to ensure that the flow rate is set to give a desired sampling rate. Controlling the pump speed results in quieter and more energy efficient operation, as well as prolonging pump life.

For the carrier gas, the mass flow controller 16 is controlled to provide optimal flows of carrier gas, to give the desired performance, during various steps of the cycle. This can improve sensitivity and repeatability, and conserve carrier gas, to give increased life time for a cylinder of argon or other inert gas.

Each cartridge 14, 15 is subjected to cycles which are short, giving small cartridge loadings, and are alternated with cleaning cycles, which automatically are performed before a calibration. Cycle times are maintained short by having a high sample gas flow rate, for example 21/min for 5, 10 or 15 minutes. It has been found that this virtually eliminates the "memory effect" previously associated with pure gold, cartridges.

Sample time, for example, flow rates and other steps in the adsorption cycle are programmable. The control circuit 130 can be set for recording two, or possibly more, complete sets of cycle parameters.

The instrument can be calibrated either by manual injection through the injection port provided at the T inlet connector 74, or alternatively, it can be automatically calibrated from the permeation source 30, allowing long term unattended operation. The source 30 can also be used at any time for manual recalibration.

While in use, the source selection valve 68 is normally switched to the sample ambient air of inlet 70. It is switched to the inlet 69 for zero air, for the following operations: cartridge cleaning operation; zero phase calibration; span phase calibration; or when the control circuit 130 otherwise switches the valve 68.

In use, with the valve 68 connected to the sample air inlet 70, air is alternately and sequentially passed through the cartridges 14, 15. The air is drawn through the cartridges by the sample pump 64.

As indicated, the lines for the air flow are relatively large, as are the valves 46 and 52, to enable a relatively large volume of air to be passed through each cartridge. Air is drawn through the cartridge 14, until the desired volume is detected by the mass flow meter 60.

Air flow is switched to the cartridge 14, at the end of the adsorption cycle for the cartridge 15. The pump 64 draws air through the cartridge 14, with the cartridge 15 being subjected to a flush and desorption cycle, detailed below. At the end of the cycle, cartridge 15 and associated dead spaces in connections to valves etc. will contain air.

After the valves 46, 52 have been switched to connect the air flow to the cartridge 14, the valves 34 and 50 are simultaneously switched to connect the cartridge 15 to the carrier gas inlet 18 and to the detector 12.

Before any gas is passed to the detector 12, the vent three-way valve 54 is switched to the vent 56.

The mass flow controller 16 is then set to a relatively high flow for a "flush" phase. This flushes out the dead volume associated with the cartridge 15 of any residual air and other impurities, typically for 20–60 seconds.

The flow is then reduced to a second, lower flow rate, which is used for the remainder of the desorption cycle. To give the flow time to stabilize, there is a measurement delay time of 1–10 seconds. This delay allows stale, possibly contaminated air to be flushed out of the cartridge before a baseline measurement is taken.

A further baseline acquisition delay, of again 1–10 seconds is then allowed, to a further stabilization of the carrier flow and flushing of the cartridge.

The second, lower flow rate is set by the mass flow controller 16, and is such as to ensure well-defined narrow peaks in the detector 12.

At the end of the flush phase, the vent three-way valve 54 is switched to connect the cartridge 15 to the detector 12.

The next step in the desorption cycle is for the instrument to make a baseline acquisition measurement. This measures the level and noise of the baseline, and can provide warning of a number of potential instrument problems. Amongst these, there are: excessive baseline shift, potentially caused by cell contamination, photo multiplier tube ageing or lamp ageing; high baseline noise, which is usually a sign of an ageing lamp. The recommended range for baseline acquisition is 5–30 seconds.

The cartridge 15 is then heated by the respective heater 41. At the start of heating, there is an integration delay, usually set in the range 10–20 seconds. This is the number of seconds between the start of heating and the activation of the peak integrator. The value should be set large enough to avoid integrating baseline noise, but small enough to ensure that the baseline immediately preceding the start of the peak is captured.

The heater on duration can be set independently for each cartridge 14, 15, in case the heaters heat at different rates. Excessive heating time may shorten the life of, or damage, the cartridges. The heating time is set to be long enough to ensure that all mercury is desorbed during each burn. As a general rule, heating should start when detector voltage stops falling after a peak, and the recommended range is 20–40 seconds.

At the end of heating, there is a peak delay time, to allow for the peak to finish eluting. During this time, the integrator is kept active. Immediately upon completion of this period, the area of the largest peak found is reported for the desorption. If the current cycle is a calibration, the appropriate correction factor is stored, while if it is an ambient run, the existing calibration correction factors are used to convert the area into a concentration.

There is then a cartridge cool down time, which is the number of seconds after expiration of the peak delay time that is required for the cartridge to cool sufficiently, and to once again adsorb mercury. Carrier gas flow rate is set at the third idle level at the start of this period. This time delays the end of the desorption cycle enough to ensure that a cartridge is always cool enough to begin sampling. During this period, the fan 42 is operated.

At the end of the cool down period, an idle time commences, during which the cartridge 15 lies idle with the third idle flow rate of carrier gas being supplied. The cartridge 15 awaits the cartridge 14 to end its sampling period. The sampling period for each cartridge cannot be set shorter than the total time required for the desorption cycle so that usually the cartridge undergoing desorption will have a certain idle period. The sampling period is recommended to be set in the range of 300–3600 seconds.

At the end of the peak delay time, the cooling fan 42 is turned on to cool the cartridge 15. Whereas fan 4 cools both cartridges 14, 15, this will not have a significant effect on the temperature of the cartridge 14, undergoing adsorption, since its temperature above ambient is small, compared to the desorption temperature.

At all times, the heaters 40, 41 are operated to maintain the cartridges at the desired minimum temperature, between ambient and about 100° C., preferably in the range 45°–75° C., with 50° C. being a normal setting.

At the end of a preset time, the cartridge 14 is fully loaded and total volume sampled is determined by integration from the flow rate served by the MFM 60. The valves 46 and 52, as well as the valves 34 and 50 are then switched. The sample air flow is then switched to the cartridge 15, and the carrier gas is switched to the first cartridge 14.

The cartridge 14 is then subjected to the same cycle sequence as outlined above.

The mass flow controller is also controlled by the control circuit 130, to maintain a third, different flow rate, during idle periods. During such periods, where no collection or detection is taking place, the carrier gas flow rate is set to a very low value to conserve carrier gas. The rate is maintained just sufficiently high enough to maintain the various lines purged, so as to prevent contamination and infiltration of air or other contaminants.

During detection, the regulator 26 provides a desired flow to the detector 12 and the permeation source 30. As described above, the flow through the detector 12, shown in FIG. 2, maintains this flushed of air, so as to give improved performance.

For the permeation source 30, this ensures that carrier gas at the desired flow rate is always available.

When the permeation source 30 is not in use, the flow restrictor 90 is connected by the valves 94, 96 to the outlet 100 and simultaneously the permeation source itself is connected through to the permeation vent 102.

Calibration of the device or apparatus 10 can be achieved by manual operation, or can be set to occur automatically at predetermined times, by the control circuit 130. During calibration, the valve 94 is activated to close off the flow to it, and the valves 96 and 98 are operated to connect the permeation chamber 84 through to the permeation outlet 100. This injects mercury at a known level or concentration into the line connected to the inlet valve 46. Simultaneously, the valve 68 will be switched to connect to a zero air inlet, so that the exact mercury concentration will be known. The detector 12 can be calibrated accordingly. As a second calibration point, a reading can be taken with the zero air, with no mercury injected.

To turn off the permeation source, for an idle state, the second permeation control valve 98 is switched back to the position connecting the permeation source to the permeation vent 102. Simultaneously, the valve 94 is opened, and the first permeation control valve 96 is closed to cut off the connection from valve 98. The valve 94 is maintained opened for a set time to flush out the line connecting source 30 to the T connector 72. Then the valve 94 is closed, so that no mercury contamination can occur from the source 30.

Calibration requires zero and span calibration points. This is usually obtained first by passing zero gas through valve 68 to the device. It then samples for one full period on each cartridge (usually 2×5=10 minutes). The area for each desorption is recorded as the expected response of the instrument when the input mercury is nil. Practically, as is well known, there is usually a small response due to residual mercury in the zero air, or due to residual contamination.

The second or span point is provided by the permeation source as indicated or by manually injecting mercury. During this phase, valve 68 is still open to feed zero air to the analyzer. Analytically, it is preferable to ensure that the zero and sampling conditions are as alike as possible. Thus, the same flow through the cartridges is maintained. Any residual mercury in the zero gas would also be present during the span phase, thus ensuring that any slope of a calibration line is unaffected. Any residual mercury in the zero gas would manifest itself as an offset in the final readings not as a sensitivity error. Further, the gas flow through the permeation source requires only a small volume of calibration gas. Zero gas is required to make up the additional volume required by the device.

The detector 12 uses cold vapour atomic fluorescence spectrophotometry for detection of mercury, since it is more sensitive and linear over a much wider range, compared to other techniques. The flushing with the carrier gas eliminates a major negative interference mode, and effectively prevents the quenching that it can cause. The ultraviolet radiation produces compounds that absorb ultraviolet light. The most important reaction is the breakdown of oxygen and the creation of free-radicals which combine with oxygen to produce ozone, which absorbs ultraviolet light. These ultraviolet absorbing compounds decrease sensitivity of the detector and cause significant baseline drift. This absorption is eliminated by the sealed detector with the purged optical path described above.

The provision of the permeation source 30 which can be automatically controlled enables the apparatus to make unattended calibrations. Known techniques rely on manual injection using gas-tight syringes, to calibrate mercury-detection instruments.

The arrangement of valve assembly 92 for the permeation source 30 ensures that even with the permeation source 30 turned off, there is no possibility of mercury leaking into the system, to contaminate subsequent samples. In the off configuration, the mercury from the permeation source passes only through the valve 98, and not through the main connection to the outlet 100, and is vented.

By maintaining the cartridges heated, it has been found that certain compounds that normally interfere with fluorescence and mercury detection in the detector cell are eliminated. The temperature is such as to prevent condensation of water and any organic compounds that may be present in the sample stream.

This has been confirmed by tests using common urban pollutants. High, although unquantified, concentrations of $H_2S$ and $SO_2$ gas were added to zero air and sampled by the analyzer. Test runs were made to confirm that these compounds cause no false positive readings. The sample air was then spiked by the injection of mercury to establish that the compounds did not cause suppression of normal readings.

The use of pure gold as an adsorption medium has often been associated with a "memory" effect, where the quantity of mercury desorbed depends upon the past history of the mercury, as well as current exposure. In effect, mercury previously adsorbed is assumed to have migrated to the interior of the gold, so that it is only released at some much later time, thereby leading to inaccuracies in later readings. Thus, a single heating cycle has been assumed to be insufficient to remove all the mercury from the gold.

Here, short cycle times are used, typically 10 minutes or less, and more preferably 5 minutes or less. This is believed to prevent the migration of the mercury from the surface of the gold.

To test the recovery rate, the device was exposed to large mercury concentrations (40–70 ng/cubic meter) for approximately 15 hours while monitoring at 10 minutes intervals. The source was provided by laboratory air spiked with additional mercury. Although the source was not accurately quantified, it was sufficiently large to exceed the upper calibration point of the instrument.

The instrument was than exposed to zero. The analyzer reported an immediate drop to less than 1% of the former readings within the first cycle. FIG. 4 summarizes this test.

The results demonstrate conclusively that the memory effect does not occur to any significant degree at the loadings and cycle times used.

It is believed that this is due to the following factors: short adsorption/desorption cycles; low mercury loadings of less than 900 pg; and incorporation of cleaning cycles to purge the cartridges before any significant operations start.

We claim:

1. An apparatus, for detecting mercury, the apparatus comprising: a main carrier inlet; a sample gas inlet; inlet valve means connected to the carrier gas and sample gas inlets; a cartridge including gold, for accumulating mercury as an amalgam, connected to the inlet valve means; an outlet valve means connected to the cartridge; a sample gas flow path extending from the sample gas inlet through the inlet and outlet valve means and through the cartridge; a pump connected to outlet valve means for pumping sample air through the cartridge in the sample gas path; a vent; a mercury detector; means for heating the cartridge to desorb mercury therein; a vent three-way valve connected to the outlet valve means and to both the detector and the vent; and a control unit connected to the inlet and outlet valve means, to the heating means and to the vent three-way valve for control thereof, wherein with the sample gas inlet and the pump connected to the cartridge by the inlet valve means and outlet valve means, the pump draws sample air through the cartridge, and with the carrier gas inlet connected by the inlet valve means through the cartridge and through the outlet valve means to the vent three-way valve, the vent three-way valve selectively connects the cartridge to one of the vent, for venting residual air, and the detector for detection of any mercury.

2. An apparatus, for detecting mercury, the apparatus comprising: a main carrier gas inlet; a sample gas inlet; two cartridges, each including gold, for accumulating mercury as an amalgam; inlet valve means connected to the carrier gas and sample gas inlets and comprising a first inlet three-way valve connected between the sample gas inlet and inlets of the two cartridges and a second inlet three-way valve connected between the carrier gas inlet and the inlets of the two cartridges; an outlet valve means connected to the cartridges and comprising a first outlet three-way valve connected between outlets of the two cartridges and a second outlet three-way valve connected between outlets of the two cartridges; a sample gas flow path extending from the sample gas inlet through the first inlet and first outlet valves and through the cartridges; a pump connected to first outlet valve for pumping sample air through the cartridge in the sample gas path; a vent; a mercury detector; means for heating the cartridges to desorb mercury therein; a vent three-way valve connected between the second outlet valve and both the mercury detector and the vent; and a control unit connected to the inlet and outlet valve means, to the heating means and to the vent three-way valve for control thereof, wherein with the sample gas inlet and the pump connected to one cartridge by the first inlet valve and first outlet valve, the pump draws sample air through the cartridge, and with the carrier gas inlet connected by the second inlet valve to one cartridge and through to the vent three away valve by the second outlet valve, the vent three-way valve selectively connects said one cartridge to one of the vent, for venting residual air, and the detector for detection of any mercury.

3. An apparatus as claimed in claim 2, which includes flow control means for controlling the carrier gas and sample gas flows.

4. An apparatus as claimed in claim 3, which includes a cooling fan means for cooling the cartridges and connected to the control unit, wherein the cartridges a e continuously heated to maintain the gold therein at a temperature above ambient temperatures and below about at 100° C., to prevent adsorption of contaminants, wherein the heating means is actuatable to selectively heat each cartridge to an elevated temperature in excess of about 500° C. to desorb mercury for detection, and subsequently the fan means is operated to cool the cartridges.

5. An apparatus as claimed in claim 3, wherein the flow control means comprises a mass flow controller connected between the carrier gas inlet and the inlet valve means, and a mass flow meter connected in the sample gas flow path, the mass flow controller and the mass flow meter being connected to the control unit.

6. An apparatus as claimed in claim 5, which includes a three-way source selection valve having an inlet connected to the sample gas inlet and another inlet for zero air, and an outlet, and a calibration source injection means connected between the outlet of the source selection valve and the first inlet three-way valve, for injection of mercury of a known concentration.

7. An apparatus as claimed in claim 6, which includes a permeation source means connected to the calibration source injection mean.

8. An apparatus as claimed in claim 7, wherein the permeation source comprises: a permeation chamber including a mercury permeation source and having an inlet and an outlet; heating means for maintaining the permeation chamber at a substantially constant temperature, connected to and controlled by the control unit; a secondary carrier gas inlet connected to the main carrier gas inlet, and to the inlet of the permeation chamber; permeation valve means connected to the outlet of the permeation chamber and to the secondary carrier gas inlet, and having a permeation source output and a permeation vent; the permeation valve means being connected to and controlled by the control unit for selectively venting the permeation chamber to the permeation vent or connecting the permeation chamber to the permeation source output.

9. An apparatus as claimed in claim 8, which includes a pressure regulator, wherein the main carrier gas inlet is connected via the pressure regulator to the secondary carrier gas inlet of the permeation source, for supply of carrier gas, and to the detector, the detector including a photomultiplier tube, a sample cuvette and an ultraviolet source, and an optical path surrounding the ultraviolet source and the cuvette, and having an optical path inlet and an optical path outlet, the optical path inlet being connected to the pressure regulator for supply of carrier gas for purging the optical path.

10. An apparatus as claimed in claim 8, wherein the permeation valve means comprises a first two-way flush valve having an outlet connected to the permeation source outlet, a permeation shut-off valve connected between the carrier gas inlet and the two-way flush valve, and a three-way permeation control valve having an inlet connected to the permeation chamber outlet, and connected to the two-way flush valve and to the permeation vent.

11. An apparatus as claimed in claim 10, which includes flow restrictors connected between the secondary carrier gas inlet and the permeation chamber inlet and the permeation valve means.

12. An apparatus for detecting mercury, the apparatus comprising: a main carrier gas inlet; a sample gas inlet; two cartridges, each including gold, for accumulating mercury as an amalgam; a first inlet three-way valve connected between the sample gas inlet and inlets of the two cartridges, and a second inlet three-way valve connected between the carrier gas inlet and the inlets of the two cartridges; a first outlet three-way valve connected between outlets of the two cartridges, and a second outlet three-way valve connected between the outlets of the cartridges; a sample gas flow path extending from the sample gas inlet through the first inlet three-way valve, one of the cartridges and the first outlet three-way valve; a carrier gas flow path extending through the second inlet three-way valve, the other cartridge and the second outlet three-way valve; a pump for pumping sample air through said one cartridge in the sample gas flow path and connected to the first outlet three-way valve; a mercury detector connected to the second outlet three-way valve, for flow of carrier gas therethrough; means, for heating each cartridge to desorb mercury therein; and a control unit connected to the first and second inlet and outlet three-way valves and to the heating means, for control thereof, wherein the cartridges can be alternately switched between the sample gas and carrier flow paths, whereby, for the one cartridge in the sample gas flow path any mercury in the sample path is adsorbed onto the gold in said one cartridge, and any mercury adsorbed onto the gold in the other cartridge, can be desorbed for detection in the mercury detector.

13. An apparatus as claimed in claim 12, which includes a three-way source selection valve having an inlet connected to the sample gas inlet and another inlet for zero air, and an outlet, and a calibration source injection means connected between the outlet of the source selection valve and the first inlet three-way valve for injection of mercury of a known concentration.

14. An apparatus as claimed in claim 13, which includes a permeation, source means connected to the calibration source injection mean.

15. An apparatus as claimed in claim 14, wherein the permeation source comprises: a permeation chamber including a mercury permeation source and having an inlet and an outlet; heating means for maintaining the permeation chamber at a substantially constant temperature, connected to and controlled by the control unit; a secondary carrier gas inlet connected to the main carrier gas inlet, and to the inlet of the permeation chamber; permeation valve means connected to the outlet of the permeation chamber and to the secondary carrier gas inlet, and having a permeation source output and a permeation vent; the permeation valve means being connected to and controlled by the control unit for selectively venting the permeation chamber to the permeation vent or connecting the permeation chamber to the permeation source output.

16. An apparatus as claimed in claim 15, wherein the permeation valve means comprises a first two-way flush valve having an outlet connected to the permeation source outlet, a permeation shut-off valve connected between the carrier gas inlet and the two-way flush valve, and a three-way permeation control valve having an inlet connected to the permeation chamber outlet, and connected to the two-way flush valve and to the permeation vent.

17. An apparatus as claimed in claim 16, which includes flow restrictors connected between the secondary carrier gas inlet and the permeation chamber inlet and the permeation valve means.

18. An apparatus as claimed in claim 17, which includes flow control means comprising a mass flow controller connected between the carrier gas inlet and the inlet valve means, and a mass flow meter connected in the sample gas flow path, the mass flow controller and the mass flow meter being connected to the control unit.

19. An apparatus as claimed in claim 18, which includes a pressure regulator, wherein the main carrier gas inlet is connected via the pressure regulator to the secondary carrier gas inlet of the permeation source, for supply of carrier gas, and to the detector, the detector including a photomultiplier tube, a sample cuvette and an ultraviolet source, and an optical path surrounding the ultraviolet source and the cuvette, and having an optical path inlet and an optical path outlet, the optical path inlet being connected to the pressure regulator for supply of carrier gas for purging the optical path.

* * * * *